United States Patent [19]

Chirife

[11] Patent Number: 5,174,286
[45] Date of Patent: Dec. 29, 1992

[54] SENSOR FOR RIGHT VENTRICULAR AND THORACIC VOLUMES USING THE TRAILING EDGE VALUE OF A GENERATED PULSE

[76] Inventor: Raul Chirife, Pirovano 137, 1640 Martinez, Buenos Aires, Argentina

[21] Appl. No.: 623,576

[22] Filed: Dec. 7, 1990

[51] Int. Cl.⁵ .......................................... A61N 1/365
[52] U.S. Cl. ............................ 128/419 PG; 128/713
[58] Field of Search ..... 128/419 D, 419 PG, 419 PT, 128/713, 734, 723

[56] References Cited

U.S. PATENT DOCUMENTS

| | | | |
|---|---|---|---|
| 3,713,449 | 1/1973 | Mulier | 128/419 PG |
| 4,141,367 | 2/1979 | Ferreira | 128/419 PT |
| 4,226,245 | 10/1980 | Bennett, Jr. | 128/419 PT |
| 4,337,776 | 7/1982 | Daly et al. | 128/419 PT |
| 4,364,396 | 12/1982 | Barthel | 128/419 PT |
| 4,674,518 | 6/1987 | Salo | 128/695 |
| 4,686,987 | 8/1987 | Salo et al. | 128/419 PG |
| 4,697,591 | 10/1987 | Likholm et al. | 128/419 PG |
| 4,719,921 | 1/1988 | Chirife | 128/419 PG |
| 4,721,110 | 1/1988 | Lampadius | 128/419 PG |
| 4,850,357 | 7/1989 | Bach, Jr. | 128/419 D |
| 4,865,036 | 9/1989 | Chirife | 128/419 D |
| 4,899,750 | 2/1990 | Ekwall | 128/419 PG |
| 4,926,862 | 5/1990 | Miyajima et al. | 128/419 D |
| 5,003,975 | 4/1991 | Hafelfinger et al. | 128/419 PT |
| 5,058,583 | 10/1991 | Geddes et al. | 128/419 D |

*Primary Examiner*—Kyle L. Howell
*Assistant Examiner*—Kennedy J. Schaetzle
*Attorney, Agent, or Firm*—Haugen and Nikolai

[57] ABSTRACT

A sensor for developing a control signal to be injected into the mechanism of a cardiac diagnosis and therapy device is disclosed. An external or internal pulse generator associated with the sensor includes a pulse width timer and an oscillator circuit to deliver constant voltage pulses through a capacitor to a lead for delivery of therapy or diagnosis. Means for detecting the peak trailing edge voltage or the current are included as an indicator of the volume of blood present in the heart or the thoracic volume at the time of stimulation. The volume signal is then directed to implantable or external devices by a control signal output to be used in the circuit of the other device.

19 Claims, 3 Drawing Sheets

SENSOR FOR RIGHT VENTRICULAR AND THORACIC VOLUMES USING THE TRAILING EDGE VALUE OF A GENERATED PULSE

BACKGROUND OF THE INVENTION

I. Field of the Invention

This invention relates generally to the design of central and peripheral sensors used in conjunction with cardiac pacemakers, monitors, drug delivery systems and other cardiac measuring devices and more particularly to a sensor for the determination of cardiac or thoracic volumes which is not dependent upon the presence of a carrier signal. It accomplishes this by determining volume as a function of the slope of capacitor discharge by measuring the trailing edge voltage (TEV) or current of the generator pulse as an indicator of load.

II. Discussion of the Prior Art

Intra-cardiac and thoracic volume measurements provide useful data for diagnosis and adaptive rate pacing. Those systems which measure intra-cardiac or intra-thoracic volume changes using impedance plesmography require the delivery of an AC or pulsed constant current carrier signal to obtain such an impedance measurement. This method has several disadvantages, including high battery drain, and somewhat complex detection algorithms.

An example of an impedance-based system is that set out in U.S. Pat. No. 4,868,987 to Salo. It uses a relatively high frequency AC carrier signal applied between spaced electrodes disposed in a beating heart. The inflow and outflow of blood in the cardiac chamber results in changes in impedance that effectively modulates the AC carrier and this modulated signal is sensed between the electrodes. This modulated carrier signal is processed to remove electrical artifacts and is then demodulated to remove the carrier frequency component. This yields an envelope which is proportional to instantaneous ventricular volume, from which a current may be derived and injected into the timing circuit of a demand-type pacemaker for changing its escape interval.

A carrier signal dependent device such as the Salo method and apparatus requires a battery to drive an oscillator which provides the necessary alternating current carrier signal to the drive electrodes. This consumes battery power, thus requiring more frequent periodic replacement or recharging.

OBJECTS

It is accordingly a principal object of the present invention to offer a new and simple method for detection of cardiac and respiratory physiological parameters which could be used for cardiac diagnosis, rate responsive pacing, drug delivery or control of an implantable cardioverter-defibrillator, using conventional pacing leads but eliminating the need for a carrier signal by using the same pulse as for pacing.

It is a further object to provide a sensor for the determination of cardiac or intrathoracic volumes that can obtain this information without the attendant battery drain of prior approaches, thus conserving battery energy, increasing battery life and decreasing the need for potentially hazardous cardiac procedures to exchange diminished batteries.

A further object is to provide such a device that may be used with standard unipolar or bipolar pacing leads.

It is still another object to avoid the need for an AC or pulsed carrier as has been required for prior art devices.

A still further object is to provide a device that is simple to implement in implantable devices.

It is an additional object to provide this device for use in diagnostic hemodynamics and adaptive rate pacing.

SUMMARY OF THE INVENTION

The foregoing objects and advantages of the invention are achieved by providing a sensor for the determination of cardiac or thoracic volumes which is independent of a carrier signal, thus ;is conservative of battery energy in a cardiac device such as a cardiac pacemaker, a cardioverter-defibrillator or an external diagnostic device or drug delivery system. Those skilled in the art will recognize that devices of this type almost universally incorporate electrical charge storage devices such as output capacitors in the pulse generating portion thereof. These capacitors may be configured to provide voltage doubling or simply to ensure that a fixed amount of charge is available for delivery to the tissue to be stimulated. At the time of stimulation, the current flowing through the lead from the output capacitor is thus a function of load. Since load is determined by the electrode-tissue interface and the volume of blood surrounding the electrodes, any change in volume would thus cause a change in current flow. Consequently, variation of load current flow on a beat-to-beat basis will be related to beat-to-beat volume changes.

Load current can be measured directly by circuitry within the pacemaker or indirectly, through secondary manifestations. Examples of indirect methods include several measurements such as pulse voltage in a constant-current pulse generator (PG), slope of coupling or output capacitor discharge, voltage of capacitor recharge pulse, trailing edge absolute voltage, or the ratio of trailing edge to leading edge.

In accordance with the present invention, trailing edge voltage (TEV), either absolute (for "in-vitro" experiments) or relative to the leading edge voltage (LEV), (for patient testings) is employed as a manifestation of load, since it can be easily externally measured in pacemakers and non-invasively recorded in patients with permanently implanted pacemakers.

Constant voltage PGs produce a square pulse delivered to the lead through a capacitor. The signal resulting from the interaction between PG output and load is a trapezoidal pulse with a leading edge voltage (LEV) representative of pacemaker output and a trailing edge voltage (TEV) dependent on battery voltage, electrode surface, capacitor value and load. Load is thus the only patient-related variable, the others being device-constants.

Research has been carried out to test the hypothesis that right ventricular and chest volume variations could produce TEV changes of diagnostic value. A bipolar lead configuration would thus be suitable for intra-cardiac measurements and a unipolar lead setup would be more appropriate for thoracic volume determination. In the case of intra-cardiac measurements, a larger blood volume with better inter-electrode conductivity, or a better thoracic conductivity (in the case of respiratory parameters), have been found to cause a steeper capacitor discharge curve with lower TEV values. During in-vitro testing, a hyperbolic relationship between volume (V) and TEV has been found. Experiments have shown that volume of fluid surrounding the pacing lead can be predicted from the value of TEV.

Thus, in accordance with my invention, one can determine the amount of energy used in capacitor discharge and use this amount as an indicator of volume displaced. A large heart would utilize a relatively larger current. Consequently, a larger volume of blood displacement correlates to a steeper decay, more current flow and thus more battery drain. Conversely, a smaller blood displacement correlates to a shallower decay, less current and less drain on the battery, enhancing its conservation.

The sensor employed utilizes standard leads, whether unipolar or bipolar. A bipolar lead is advantageous for cardiac measurements because it is subject to little influence by external parameters such as chest volume or conductivity changes. In contrast, the unipolar configuration is subject to chest conductivity changes, such as those concomitant with normal breathing.

Assuming that a stimulator with a constant voltage pulse generator is involved, the present invention utilizes trailing edge voltage (TEV) as an indicator of cardiac or respiratory volume. When capacitor discharge is plotted against time, a characteristic slope in current is obtained. The square wave stimulus that is introduced to a coupling capacitor is altered by cardiac structures to produce a signal in which the leading edge has a higher voltage than the trailing edge. The resultant trailing edge voltage is proportional to intracardiac or thoracic volume, depending upon the lead configuration used. Those skilled in the art will appreciate that if a constant current pulse generator is involved, it is possible to measure the voltage variations resulting from the changes in load impedance as blood flows in and out of the heart.

DESCRIPTION OF THE DRAWINGS

The foregoing features, objects and advantages of the invention will become apparent to those skilled in the art from the following detailed description of the preferred embodiment, especially when considered in conjunction with the accompanying drawings.

DESCRIPTION OF THE PREFERRED EMBODIMENT

Figure 1:
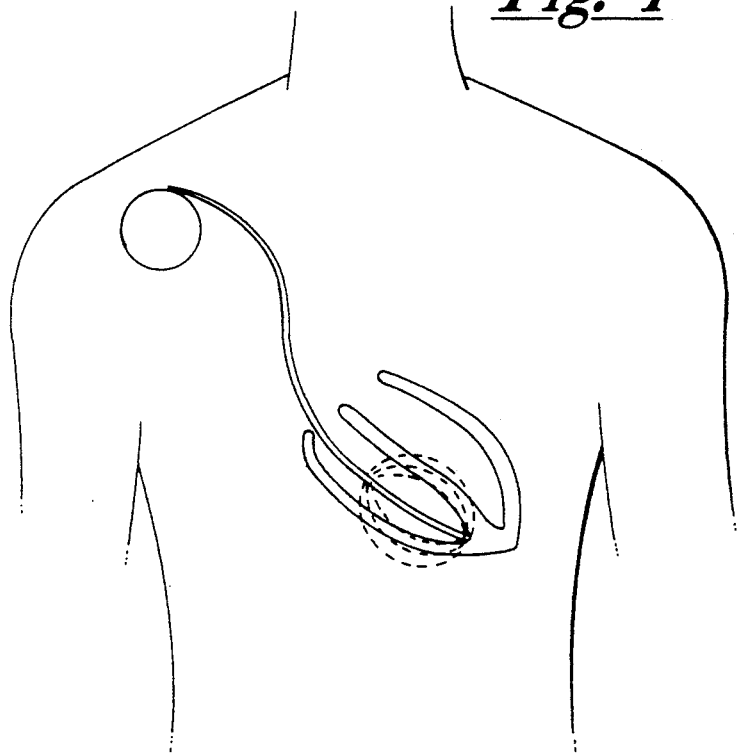
FIG. 1 depicts sensor using a bipolar lead configuration placed in the apex of the right ventricle.

The sensor of the present invention may be used in conjunction with standard lead types known in the art. FIG. 1 depicts a standard bipolar lead configuration for intra-cardiac measurements that would be suitable for use with the present sensor mechanisum. In such a lead, the rhythm managing stimulus is primarily modified by cardiac volume. Chest volume variations or conductivity variations have practically no influence on the waveform produced.

Figure 2:
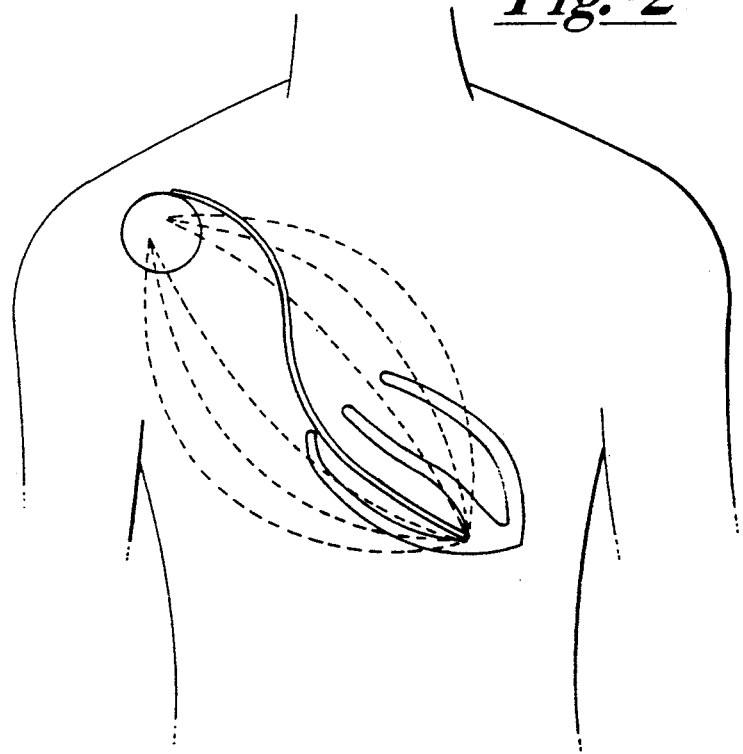
FIG. 2 depicts sensor using a unipolar lead configuration to deliver a pacing stimulus at the apex of the right ventricle.

Alternately, a standard unipolar lead may be used in conjunction with the TEV sensor of the present invention, as depicted in FIG. 2. This lead setup would be more appropriate for thoracic volume determination, since the can of the pacemaker is used as the indifferent electrode and a more global influence occurs. In this configuration, chest conductivity changes, especially those produced by breathing, affect the stimulator's output capacitor discharge, producing TEV modifications which have been found to correspond to respiratory amplitude and frequency of ventilation. From such a configuration, it is possible to measure tidal volume, and derive from this an indication of minute ventilation using the product of tidal volume and respiratory rate.

Figure 3:
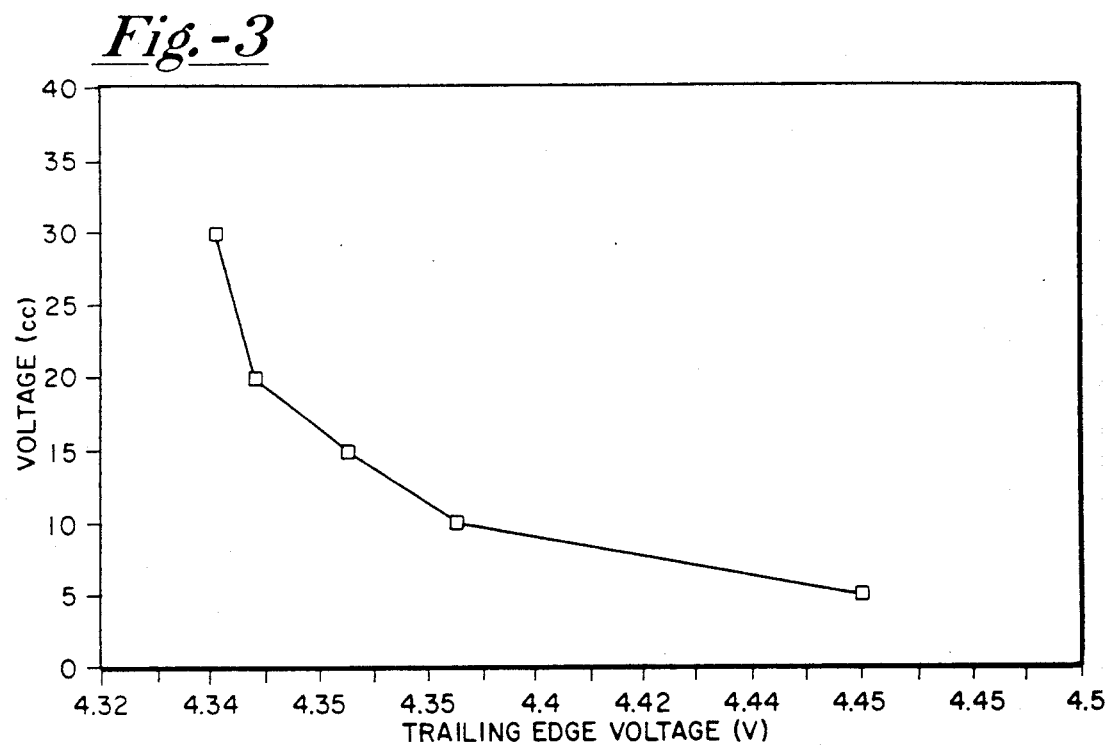
FIG. 3 is a graph which depicts the dependent relationship between trailing edge voltage of a stimulator output capacitor and volume.

The sensor of the present invention is based upon the principle that a hyperbolic relationship exists between volume (V) and trailing edge voltage (TEV) for both intra-cardiac and thoracic volume changes. FIG. 3 depicts this relationship for the voltage range commonly used in cardiac devices.

Several factors have been found to affect this relationship. The present invention centers on the realization that TEV is dependent upon battery voltage, electrode surface, capacitor value and load. All except load are device constants, with load determined by the characteristics of the patient. The load encountered at each sampling is thus a significant influence upon the amount of current used.

Figure 4:
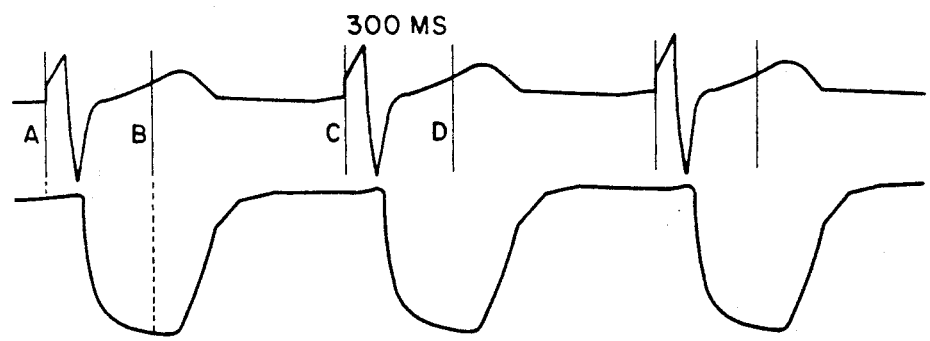
FIG. 4 depicts the interrelationship between TEV and the cardiac cycle when responding to pacing stimuli at various times.

FIG. 4 depicts the interrelationship between TEV and the cardiac cycle. It has been determined that measurement of TEV with bipolar leads may be done anywhere within the cardiac cycle. If measurements are carried out only on the pacing stimuli, the volume estimation will be based on that point of the cardiac cycle corresponding to end-diastole, i.e., end-diastolic volume (EDV). By comparing EDV on a beat-by-beat basis, changes in end-diastolic volume due to metabolic demands can be detected. This beat-to-beat variation can thus be used as a signal indicative of hemodynamic status or to drive a rate responsive pacemaker in the standard manner.

If a second stimulus is delivered approximately 300 msec after the first, within the ventricular refractory period, and preferably of sub-threshold voltage, an estimation of end-systolic volume (ESV) may be obtained (FIG. 4). The second stimulus may be below capturing threshold, since the effect on the TEV is independent from capture. The first stimulus is used to allow TEV to be measured at end-diastolic volume and the second used to measure TEV at end-systolic volume. The difference between the end-diastolic and end-systolic volumes gives a measure of stroke volume (SV). This signal has many diagnostic and therapeutic implications. If the value of SV is multiplied by heart rate, cardiac output (CO) is obtained. This signal is very valuable in the clinical management of patients with cardiac insufficiency. If SV is considered on its own, rate control can be implemented. It is also possible to use ESV by itself as a diagnostic hemodynamic parameter for rate control when beat-to-beat comparisons are made.

Figure 4A:
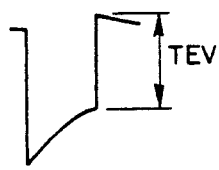
FIGS. 4A and 4B illustrate TEV in response to pulses at points A and B, respectively, as shown in FIG. 4.
Figure 4B:
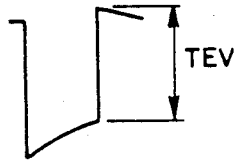

Referring to FIG. 4, the upper plot depicts a standard electrocardiogram signal throughout three normal cardiac cycles wherein FIGS. 4A and 4B illustrate TEV in response to pulses at points A and B, respectively. Points A and C mark a pacing spike. This spike causes the onset of a standard QRS depolarization, thus points A and C also indicate points of largest end-diastolic volumes for their respective cycles. The lower plot depicts change in TEV with time. Thus, points A and C also correspond to points of high TEV. Points B and D denote noncapturing spikes delivered 300 msec after the capturing spikes A and C. They correspond to points of end-systolic volume and low TEV. Stroke volume may be calculated by subtracting the volume measurement for B from A and for D from C. Cardiac output may be obtained from the product of heart rate times stroke volume (CO=HR×SV). Right ventricular ejection fraction (EF) can be calculated as the ratio SV/EDV. Referring to FIG. 4, ejection fraction may be determined by subtracting the volume at D from that at C then dividing by the volume at C and multiplying the result by 100. This physiologic signal is quite independent from pre-load and is a good index of contractility, applicable for diagnosis and adaptive rate pacing.

As indicated above, measurement of respiratory parameters is also possible, using a standard unipolar lead. If TEV is measured with a standard unipolar lead, it will be influenced to a greater extent by changes in the thoracic conductivity and volume rather than by cardiac events. Measurements done in patients with unipolar leads revealed concordance of changes in TEV with the phases of respiration. Since normally there is a 6:1 relationship between heart rate and respiratory rate, at least 6 samples in each respiratory cycle could be obtained, which allows an estimation not only of respiratory rate (RR) but also of respiratory tidal volume (TV). The product of both is the minute-ventilation (MV), defined as MV=TV×RR.

Figure 5:
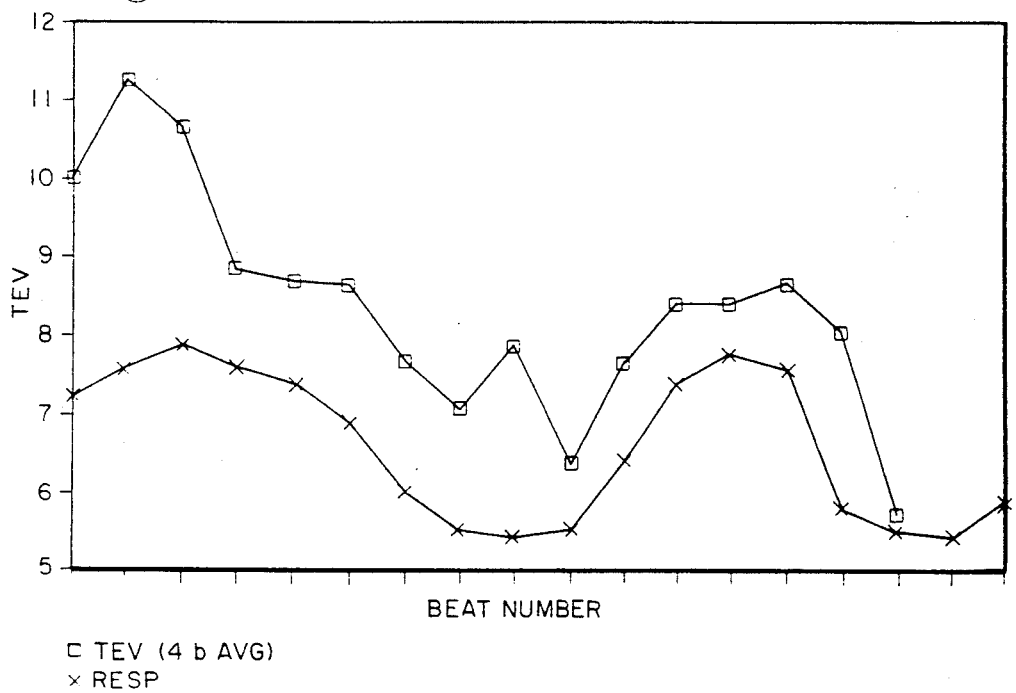
FIG. 5 presents a plot of TEV during different phases of respiration in a patient with a unipolar lead.

FIG. 5 shows the relationship between the phases of respiration and measured TEV. Upgoing portions of the respiration curve indicate inspiration. The plotted TEV values may be calculated as 4-beat averages which were used to smooth-out measurement errors.

Figure 6:
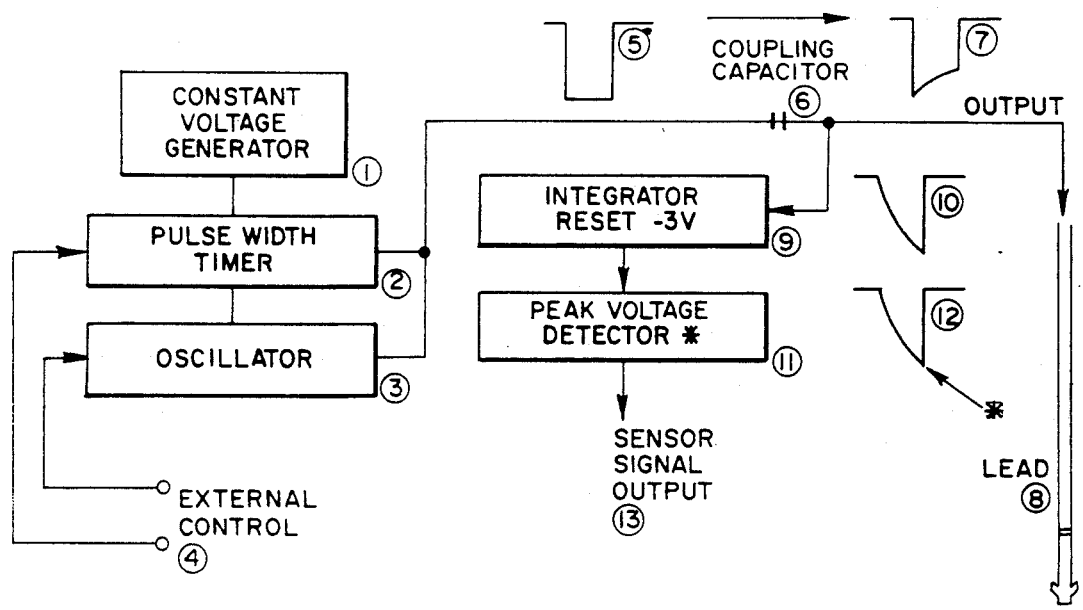
FIG. 6 is a block diagram of the circuitry required to implement a TEV sensor of the present invention.

Referring now to FIG. 6, the sensor circuitry which may be incorporated into implantable rhythm control devices (pacemakers and cardioverter-defibrillators) or external diagnostic or drug delivery devices is shown by means of a block diagram.

FIG. 6 should be considered only as an example of several ways in which the detection of the capacitor discharge slope can be implemented. The stimulator comprises a conventional combination oscillator 3. The oscillator 3 produces as square wave pulse 5 having a width controlled by time 2 and which is directed to the intra-cardiac lead 8 via a coupling or output capacitor 6. Due to the above mentioned interaction between the pulse generator output and cardio-thoracic structures, a change in the stimulus waveform takes place, whereby the leading edge has a higher voltage than the trailing edge, as seen at 7. In accordance with this invention, this signal 7 is direction to and sensed by an integrator 9 having a reset voltage set at a percentage of the trailing edge. For example, a reset of 60% or −3 V, for a conventional pulse generator output of 5 V is suggested. The resulting integrated signal is depicted at 10. The purpose of the integrator is to simplify the peak voltage detection of the next stage 11 which detects the maximum voltage achieved as shown by the arrow at 12, and represents the value of the trailing edge voltage, TEV.

The resulting voltage is directed to the output of the sensor on line 13, either in analog or digital format, to be used by the above mentioned pacemaker, cardioverter-defibrillator, drug delivery system or external diagnostic device. In the case of a rate responsive pacemaker, the voltage on line 13 may comprise a pacing rate control signal which is fed to external control inputs 4 for adjusting either the pacer pulse width or the stimulation frequency.

This invention has been described herein in considerably detail in order to comply with the Patent Statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

I claim:

1. Apparatus for applying therapy to a patient, comprising in combination:
    (a) pulse generator means for producing square wave pulses;
    (b) stimulating lead means for applying stimulating pulses to body tissues;
    (c) capacitor means connected to said pulse generator means for delivering said square wave pulses to said lead means;
    (d) integrator means coupled to said capacitor means for determining a parameter of a trailing edge signal resultant from said square wave pulses, said integrator means including a reset means for terminating integration of said trailing edge signal;
    (e) peak detector means connected to said integrator means for detecting a maximum value achieved of said parameter of said trailing edge signal; and
    (f) means connected to said peak detector means for outputting the peak detected maximum value.

2. The apparatus as in claim 1, wherein said reset means includes means for removing antifact by developing a control signal from a fixed percentage of said square wave pulse.

3. Apparatus for applying therapy to a patient, comprising in combination:
    (a) pulse generator means for producing square wave pulses;
    (b) stimulating lead means for applying stimulating pulses to body tissue;
    (c) capacitor means connected to said pulse generator means for delivering said square wave pulses to said lead means;
    (d) integrator means coupled to said capacitor means for determining a trailing edge voltage resultant form said square wave pulses, said integrator means including a reset means for terminating integration of said trailing edge voltage;
    (e) voltage peak detector means connected to said integrator means for detecting the maximum voltage achieved for said trailing edge voltage; and
    (f) means connected to said voltage peak detector means for outputting the peak detected trailing edge voltage signal.

4. The apparatus as in either claim 1 or claim 3 wherein said stimulating lead means is a bipolar lead.

5. The apparatus as in either claim 1 or claim 3, wherein said stimulating lead means is a unipolar lead.

6. The apparatus as in claim 3, wherein said reset means includes means for removing antifact by developing a control signal from a fixed percentage of said square wave pulse.

7. A method of producing a control signal for an apparatus for applying treatment to a patient comprising:
  (a) producing an output signal pulse;
  (b) applying said output signal pulse to tissue of the patient to be stimulated by way of a coupling capacitor and a stimulating lead;
  (c) sensing a parameter of a trailing edge signal resultant from said output signal pulse developed across said coupling capacitor; and
  (d) using the sensed parameter of the trailing edge signal to determine an intracardiac volume of the patient.

8. A method as in claim 7 wherein said treatment is cardiac pacing.

9. A method as in claim 7 wherein said treatment is drug delivery.

10. The method of claim 7 further comprising the step of:
  (e) using the sensed parameter of the trailing edge signal to determine an intrathoracic volume of the patient.

11. In an implantable cardiac rhythm management device of the type comprising pulse generating means for producing output pulses and means including an output capacitor and a pacing lead for coupling said output pulses to tissue of a patient to be stimulated, said device including an improved physiologic sensor comprising:
  (a) means for deriving a control signal corresponding to a parameter of a trailing edge signal resultant from the pulse signals applied to said tissue; and
  (b) means for determining an intracardiac volume of a patient the device is adapted to as a function of said control signal and providing a first output indicative thereof.

12. The device as specified in claim 11 wherein said determining means further comprises means for determining stroke volume of a heart of the patient the device is adapted to as a function of said first output.

13. The device as specified in claim 11 wherein said determining means further comprises means for determining cardiac output of a heart of the patient the device is adapted to as a function of said first output.

14. The device as specified in claim 11 wherein said determining means further comprises means for determining ventricular ejection fraction of a heart of the patient the device is adapted to as a function of said first output.

15. In an implantable cardiac rhythm management device of the type comprising pulse generating means for producing output pulses and means including an output capacitor and a pacing lead for coupling said output pulses to tissue of a patient to be stimulated, said device including an improved physiologic sensor comprising:
  (a) a means for deriving a control signal corresponding to a parameter of a trailing edge signal resultant from the pulse signals applied to the tissue; and
  (b) means for determining a thoracic volume of a patient the device is adapted to as a function of said control signal and providing a first output indicative thereof.

16. The device as specified in claim 11 or 15 wherein said determining means adjusts a characteristic of said output pulses from said pulse generating means as a function of said first output.

17. The device as specified in claim 15 wherein said determining means further comprises means for determining tidal volume of the patient the device is adapted to as a function of the first output.

18. The device as specified in claim 15 wherein said determining means further comprises means for determining minute ventilation of the patient the device is adapted to as a function of the first output.

19. A method of cardiac monitoring a patient comprising:
  (a) producing an output signal pulse;
  (b) applying said output signal pulse to tissue of the patient to be stimulated by way of a coupling capacitor and a stimulating lead;
  (c) sensing a parameter of a trailing edge signal resultant from said output signal pulse developed across said coupling capacitor;
  (d) using the sensed parameter of the trailing edge signal to determine an intracardiac volume of the patient; and
  (e) producing a first output signal indicative of the determined intracardiac volume for monitoring of the patient.

* * * * *

UNITED STATES PATENT AND TRADEMARK OFFICE
CERTIFICATE OF CORRECTION

PATENT NO.  : 5,174,286
DATED       : December 29, 1992
INVENTOR(S) : Raul Chirife It is certified that error appears in the above-identified patent and that said Letters Patent is hereby corrected as shown below:

COLUMN 6, LINE 3,

Claim 3, letter (d), after the word "resultant", the word "form" should be changed to -- from --

Signed and Sealed this

Second Day of November, 1993

Attest:

BRUCE LEHMAN

Attesting Officer

Commissioner of Patents and Trademarks